US007534336B2

(12) United States Patent
Volkel et al.

(10) Patent No.: US 7,534,336 B2
(45) Date of Patent: May 19, 2009

(54) CONTINUOUS FLOW PARTICLE CONCENTRATOR

(75) Inventors: Armin R. Volkel, Mountain View, CA (US); Meng H. Lean, Santa Clara, CA (US); H Ben Hsieh, Mountain View, CA (US); Jurgen H Daniel, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 920 days.

(21) Appl. No.: 10/838,570

(22) Filed: May 4, 2004

(65) Prior Publication Data

US 2005/0247564 A1 Nov. 10, 2005

(51) Int. Cl.
*G01N 27/453* (2006.01)

(52) U.S. Cl. ........................................ 204/643; 204/600

(58) Field of Classification Search ................. 204/450, 204/603, 547, 643
See application file for complete search history.

(56) References Cited

U.S. PATENT DOCUMENTS

| | | | | |
|---|---|---|---|---|
| 5,632,957 A | 5/1997 | Heller et al. | 422/68.1 |
| 5,653,859 A | 8/1997 | Parton et al. | 204/450 |
| 6,013,165 A * | 1/2000 | Wiktorowicz et al. | 204/456 |
| 6,272,296 B1 | 8/2001 | Gartstein | 399/55 |
| 6,355,491 B1 | 3/2002 | Zhou et al. | 436/518 |
| 7,156,970 B2 | 1/2007 | Lean et al. | |
| 7,163,611 B2 | 1/2007 | Volkel et al. | |
| 7,282,129 B2 | 10/2007 | Lean et al. | |
| 2004/0038249 A1 * | 2/2004 | Darteil et al. | 435/6 |

OTHER PUBLICATIONS

Dunphy et al. "Rapid Separation and Manipulation of DNA by a Ratcheting Electrophoresis Microchip (REM)," Proceedings of IMECE2002, Nov. 17-22, 2002, New Orleans, LA., No. IMECE2002-33564.

U.S. Appl. No. 10/460,137 entitled "Traveling Wave Algorithms to Focus and Concentrate Proteins in Gel Electrophoresis"to Meng H. Lean et al., filed Jun. 12, 2003.

U.S. Appl. No. 10/459,799 entitled "Distributed Multi-segmented Reconfigurable Traveling Wave Grids for Separation of Proteins in Gel Electrophoresis" to Meng H. Lean et al., filed Jun. 12, 2003.

U.S. Appl. No. 10/727,289 entitled "Concentration and Focusing of Bio-agents and Micron-Sized Particles Using Traveling Wave Grids" to Armin R. Volkel et al., filed Dec. 3, 2003.

U.S. Patent Application entitled "Portable Bioagent Concentrator" to H. Ben Hsieh et al., filed May 4, 2004.

* cited by examiner

*Primary Examiner*—Alex Noguerola
(74) *Attorney, Agent, or Firm*—Fay Sharpe LLP

(57) ABSTRACT

An apparatus for extracting and concentrating bioagents within a continuously flowing fluid medium includes a flow channel fluid inlet, in which bioagents are concentrated from three dimensions to a two-dimensional transport layer in a preconcentration area. Traveling wave grids cause the pre-concentrated bioagents to migrate to one side of the flow channel and then to an extraction port. Each of the traveling wave grids includes a substrate, a collection of closely spaced and parallel electrically conductive electrodes extending across said substrate, and a collection of buses providing electrical communication with the collection of conductive electrodes. A voltage controller provides a multiphase electrical signal to the collection of buses and electrodes of the traveling wave grids. Fluid exits through an outlet port.

24 Claims, 7 Drawing Sheets

CONTINUOUS FLOW PARTICLE CONCENTRATOR

This work was funded in part by the Department of Defense, Army Research Office (DOD ARO) under contract DAAD19-03-C-0116. The U.S. Government may have certain rights in this invention.

CROSS REFERENCE TO RELATED APPLICATIONS

The following copending applications, U.S. application Ser. No. 10/460,137, filed Jun. 12, 2003, titled "Traveling Wave Algorithms to Focus and Concentrate Proteins in Gel Electrophoresis", U.S. application Ser. No. 10/459,799, filed Jun. 12, 2003, titled "Distributed Multi-segmented Reconfigurable Traveling Wave Grids for Separation of Proteins in Gel Electrophoresis", U.S. application Ser. No. 10/727,289, filed Dec. 3, 2003, titled "Concentration and Focusing of Bio-agents and Micron-sized Particles Using Traveling Wave Grids", and U.S. application Ser. No. 10/838,937, filed May 4, 2004, titled "Portable Bioagent Concentrator", are assigned to the same assignee of the present application. The entire disclosures of these copending applications are totally incorporated herein by reference in their entirety.

INCORPORATION BY REFERENCE

The following U.S. patents are fully incorporated herein by reference: U.S. Pat. No. 5,632,957 to Heller et al. ("Molecular Biological Diagnostic Systems Including Electrodes"); U.S. Pat. No. 6,272,296 to Gartstein ("Method and Apparatus Using Traveling Wave Potential Waveforms for Separation of Opposite Sign Charge Particles"); and U.S. Pat. No. 6,355,491 to Zhou et al. ("Individually Addressable Micro-electromagnetic Unit Array Chips").

BACKGROUND

This disclosure relates generally to the field of electrophoretic separation of bio-agents and particles, and more particularly, to systems and devices for focusing the bio-agents into regions of relatively high concentrations.

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarizable particle in a non-uniform electric field. Essentially, the force arises from the interaction of the field non-uniformity with a field induced charge redistribution in the separated particle.

Particles are manipulated using non-uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, a need for improved strategies and methodologies remains. In addition, dielectrophoresis requires higher voltage (~100 V), higher frequencies (~10 MHZ), and finer electrode pitch (<10 um).

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17-22, 2002, New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory equipment. Accordingly, a need exists for a device and technique for utilizing electrostatic traveling waves for selectively concentrating bio-agents and particles, and particularly, for subsequent analysis.

Bio-agents dispersed either in aerosol form or in water are typically in such low concentrations that they are below the limit of detection (LOD) of even the most sensitive detection schemes. Yet, the ingestion of even a single bacterium may lead to fatal consequences. Aerosol collection schemes typically sample large volumes of air at very high rates (up to 150 kl/min), and use a cyclone or a virtual impactor to collect particles of size in the threat range and capture them in a wet sample of 5-10 ml volume. This hydrosol is then used as the test sample for agent detection.

Contaminants in water are typically treated by several filtration steps to recover the sample for agent testing. After initial pre-filtration to remove large, vegetative matter, the sample is further concentrated by two to three orders of magnitude using ultra-filtration. This method of tangential flow filtration (TFF) is laborious as it requires multiple sequential steps of TFF; each step with a filter of lower molecular weight cut-off, and recycling of the retentate. The supernatant at the end is the 50 ml volume to be presented to the detector. Regardless of whether the sample is derived from aerosol or water collection, it would be useful to have a device to further concentrate the sample prior to detection, preferably by several orders of magnitude and within a smaller volume in the 50-100 μl range.

BRIEF SUMMARY

The disclosed embodiments provide examples of improved solutions to the problems noted in the above Background discussion and the art cited therein. There is shown in these examples an improved apparatus for extracting and concentrating bioagents within a continuously flowing fluid medium. The apparatus includes a flow channel fluid inlet, in which bioagents are concentrated from three dimensions to a two-dimensional transport layer in a preconcentration area. Traveling wave grids cause the preconcentrated bioagents to migrate to one side of the flow channel and then to an extraction port. Each of the traveling wave grids includes a substrate, a collection of closely spaced and parallel electrically conductive electrodes extending across said substrate, and a collection of buses providing electrical communication with the collection of conductive electrodes. A voltage controller provides a multiphase electrical signal to the collection of buses and electrodes of the traveling wave grids. Fluid exits through an outlet port.

BRIEF DESCRIPTION OF THE DRAWINGS

The foregoing and other features of the embodiments described herein will be apparent and easily understood from a further reading of the specification, claims and by reference to the accompanying drawings in which:

DETAILED DESCRIPTION

The continuous flow particle concentrator uses electrostatic fields and traveling wave grids to extract charged bio agents, such as bio-molecules, viruses, bacteria, etc., from a large volume of liquid (up to many liters) and concentrate or focus them into a small volume (several cubic millimeters) for detection. To allow for continuous screening, the extraction process takes place while the liquid is flowing through a channel. Bio matter is initially deposited onto a surface patterned with a planar inter-digitated electrode grid. The inter-digitated electrodes are driven in 4-phase (or n phases with n>2) with a traveling wave (TW) of voltage pulses to move the deposited biomatter to an edge where another orthogonal TW array moves the bio matter to a sample well, resulting in concentration of several orders of magnitude, thus increasing sensitivity for bio-agent detection. The concentrator may be utilized for all material with a net charge and may serve either as a supplementary concentration step in a concentration process or to supply concentrated materials to a detection device. Depending on the size of the bio agents that are collected, the particles may be concentrated into an area with a higher (effective) viscosity medium, such as a gel, before being focused and delivered to a detector or array of detectors. This will reduce thermal diffusion, which becomes a dominant dynamic factor for sub-micron particles. For example, particles in the range of 1-10 μm may be captured either with or without the presence of a gel. Particles in the range of 10-100 nm would probably require use of a gel. For the purposes of clarity, the embodiments discussed herein are described as operating on a liquid sample. However, it is noted that these embodiments could also be beneficially utilized for the concentration of particles in aerosol samples, with all such uses fully contemplated by the specification and scope of the claims herein.

Figure 1:
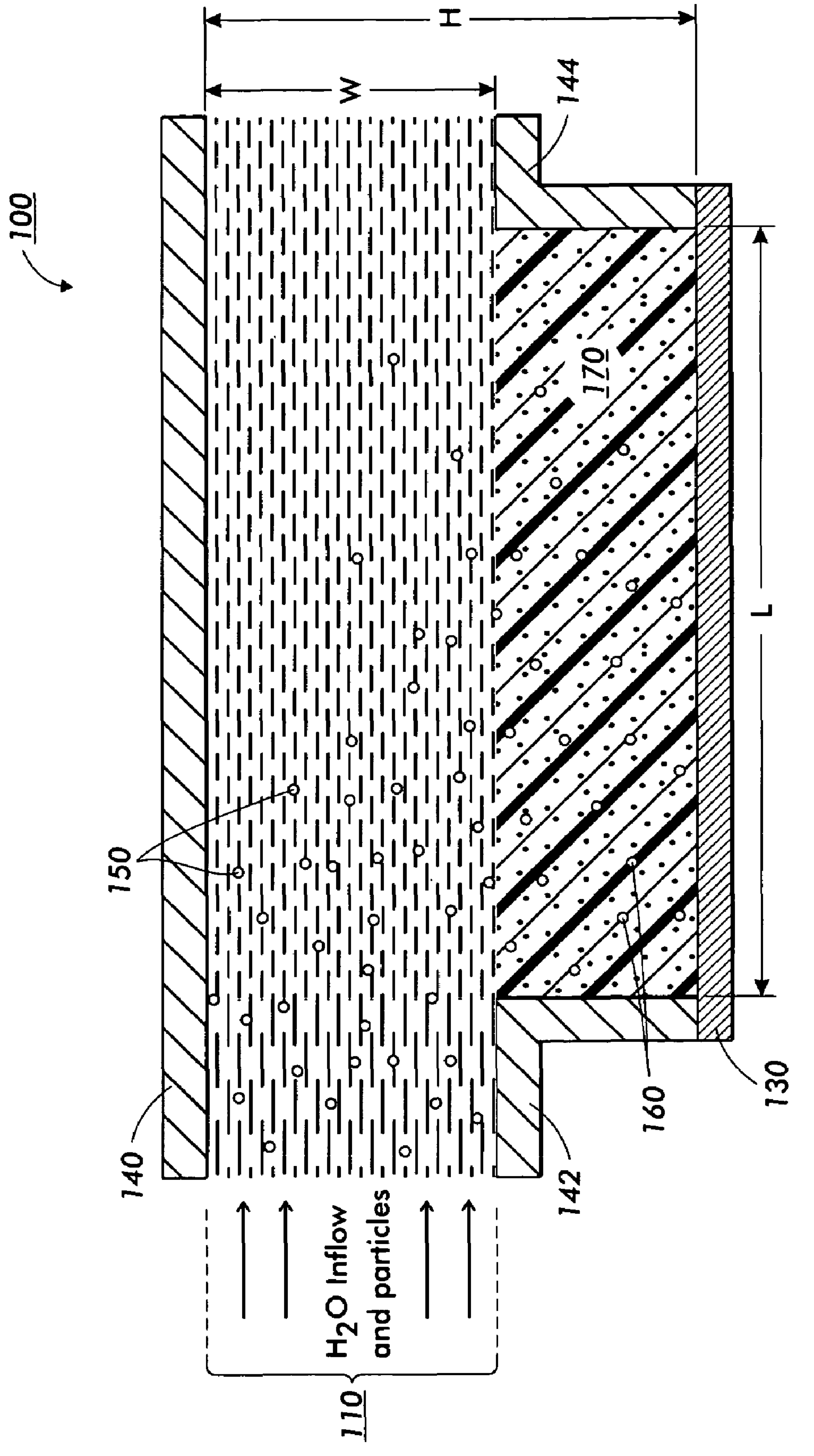
FIG. 1 is a schematic illustration of one embodiment of the continuous flow particle concentrator.

FIG. 1 shows a schematic drawing of a top view of one example embodiment of the particle concentrator. In this embodiment, a liquid is passed left to right through a flow channel of width W, whose inlet 110 is formed by walls 140 and 142 and whose outlet is formed by walls 140 and 144. Charged bio-agents 150 are removed from the liquid by concentrating them into a thin "transport" layer at the bottom of channel 110. This concentration from three to two dimensions may be achieved by use of electrostatic forces, hydrodynamic forces, geometric constraints, or a combination of any or all of these. The height of this transport layer depends on the reach of the traveling wave grid and is approximately the same as the electrode spacing of the grid.

Once the particles are concentrated within the transport layer, they pass across a traveling wave grid (not shown) having a length L and height H and which moves the particles to one side of the channel, as further described in U.S. patent application Ser. No. 10/727,289, "Concentration and Focusing of Bio-agents and Micron-sized Particles Using Traveling Wave Grids". The traveling wave grid includes a substrate, a collection of closely spaced and parallel electrically conductive electrodes extending across the substrate, and a collection of buses providing electrical communication with the collection of electrodes. At this location the particles 160 may be trapped into high-viscosity medium 170, although the device may be operated without the presence of high-viscosity medium 170. High-viscosity medium 170, perhaps in the form of a gel, is a porous, but solid, material that retains its shape independent of the liquid flowing by in the channel. Although some exchange of liquid between the channel and the liquid trapped inside the gel layer may occur, the gel will prevent the formation of vortices or convective flow patterns that may overwhelm the electrostatic forces that move the bio agents into the gel layer.

An additional traveling wave grid 130 (shown here in cross-section), oriented approximately orthogonally to the first grid, can then further focus the bio-agents trapped in high viscosity medium 170 and move them to a detector or array of detectors (not shown). The second traveling wave grid includes a substrate, a plurality of closely spaced and parallel electrically conductive electrodes extending across the substrate, and a collection of buses providing electrical communication with the collection of electrodes on the substrate of the second traveling wave grid.

Also included but not shown are at least one voltage controller which provides a multi-phase electrical signal to the collection of buses and electrodes of both the first and second traveling wave grids. The voltage controller is configured to apply the control signal to the first traveling wave grid and the second traveling wave grid such that the bio-agent particles within the fluid medium at least partially travel or migrate across the first traveling wave grid in a direction generally perpendicular to the direction of the electrodes of that first grid. Then the bio-agents further migrate through the fluid medium at least partially across the second traveling wave grid in a direction generally perpendicular to the direction of the second collection of electrodes disposed on the second traveling wave grid. By use of this system and preferably in this manner, a bio-agent or collection of bio-agents, or collection of particles, can be directed or focused into a relatively highly concentrated region. The structure and relationship of the approximately orthogonal traveling wave grids are described in more detail with reference to FIG. 6 herein below.

Figure 2:
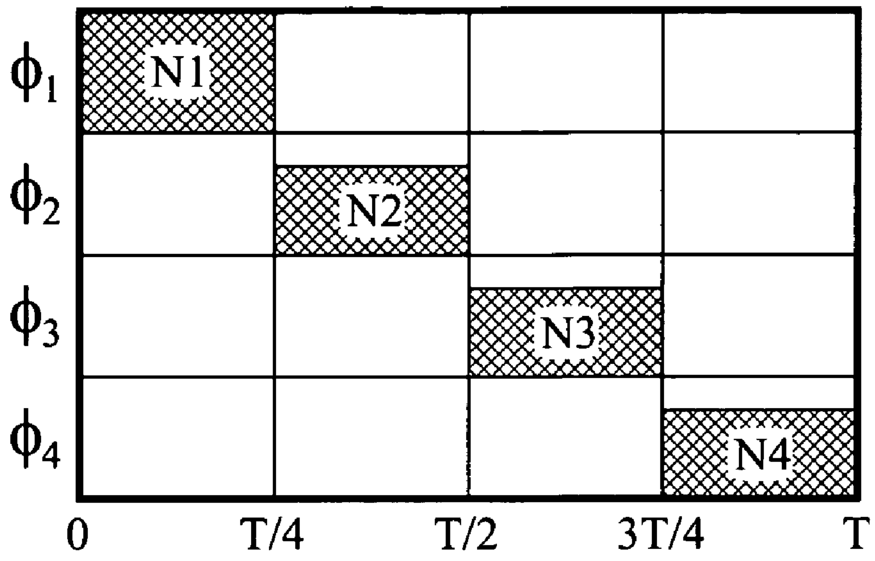
FIG. 2 is a representative four phase traveling wave voltage pattern employed in the traveling wave grids.

FIG. 2 is a representative four-phase voltage pattern or waveform used in the example embodiment systems and traveling wave grids of the particle concentrator. For the purposes herein, the four phase voltage waveform has a 90 degree separation between phases. Each waveform occurring in each phase is a square wave pulse, with each pulse sequentially applied to an adjacent electrode. Thus, a first pulse in phase N1 is applied to a first electrode for a desired time period, such as T/4. Upon completion of that first pulse, such as at time T/4, a second pulse in phase N2 is applied to a second electrode, which may be immediately adjacent to the first electrode. Upon completion of that second pulse, such as at time T/2, a third pulse in phase N3 is applied to a third electrode, which may be adjacent to the second electrode. Upon completion of that third pulse, such as at time 3T/4, a fourth pulse in phase N4 is applied to a fourth electrode, which may be adjacent to the third electrode. This sequential and ordered array of voltage pulsing results in bio-agents or particles dispersed in the liquid to "hop" from the vicinity of one electrode to another.

Figure 3:
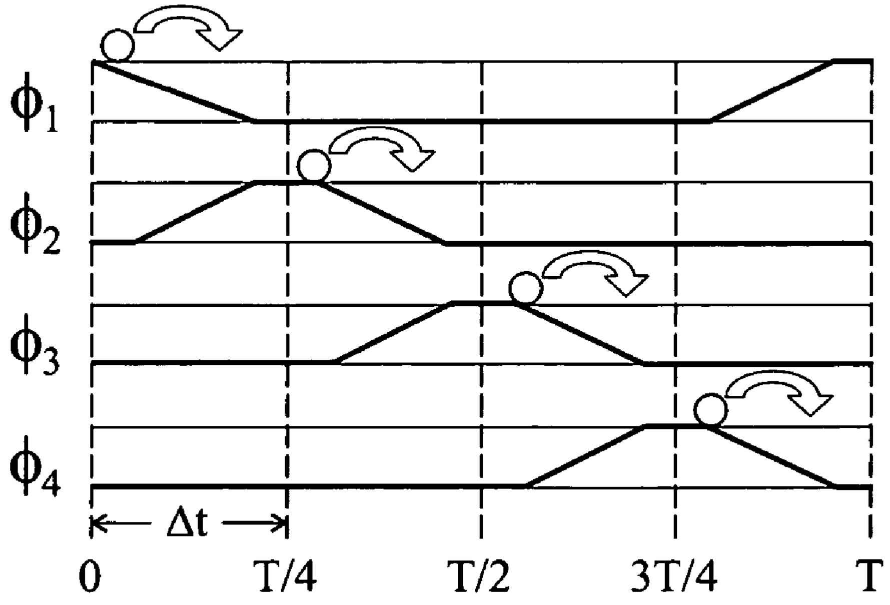
FIG. 3 is a schematic illustration of biomolecule transport from one electrode to another.

The synchronous mode of propagation is depicted in FIG. 3 and may be described as a "hopping" mode where the bio-agent or particles hop from electrode to electrode in the direction of the pulse train. The transit time to migrate across the dielectric space is then given by:

$$t_{transit}=s/\mu E,$$

where pitch is given by p=w+s, and w and s are the electrode width and dielectric space, respectively. Electric field and mobility are given by E and μ, respectively. The period for one cycle through the four phases is $4*t_{transit}$, so that the maximum sweep frequency is:

$$f<\mu E/4s.$$

For sustained transport, the bio-agent or particle has to have sufficient speed (μE) and time ($t_{transit}$) to traverse the distance of the dielectric space, s. This equation implies that for sustained transport, there is a critical frequency for bio-agents or particles of a certain mobility. In order to concentrate all bio agents from the channel, the TW grid has to be operated at a frequency that allows transportation of the slowest particle.

Figure 4:
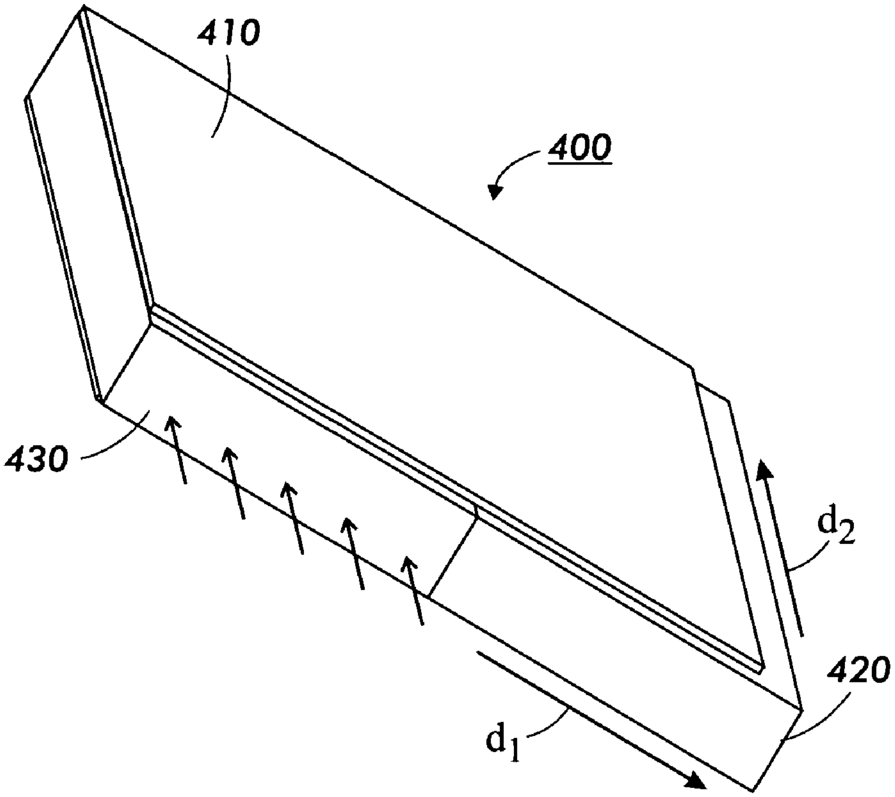
FIG. 4 is a perspective illustration of the particle concentrator fluid flow patterns for the embodiment of FIG. 1.

Turning now to FIG. 4, there is provided a three-dimensional view of one embodiment of the particle concentrator. Water and bioagents, which have been pre-concentrated, flow through channel passage 430 and parallel with the traveling wave grid 410 until they are in position over the grid 410. Application of a traveling wave moves the bio particles in a first concentration direction $d_1$ toward a second traveling wave grid 420. Traveling wave grid 420 then causes the particles to move in a second concentration direction $d_2$ toward a detector (not shown).

Figure 5:
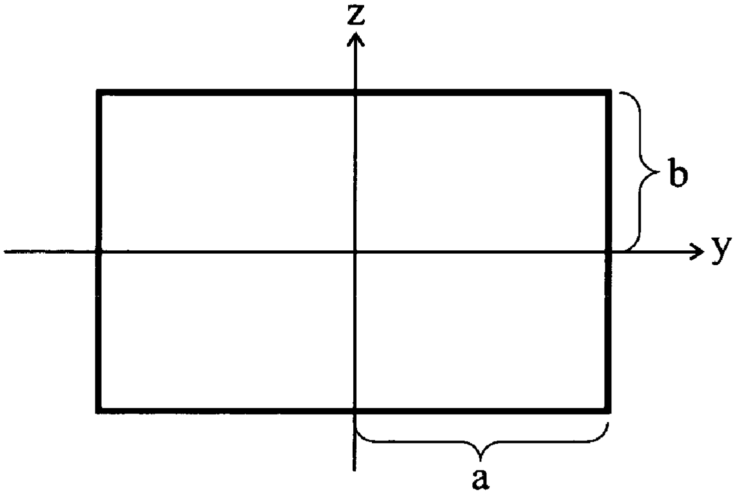
FIG. 5 illustrates the flow channel cross-section for the embodiment of FIG. 1.

The speed with which particles can be extracted from the probe liquid depends on many parameters, including channel geometry, mobility of bio-agents, and applied electric fields. The channel cross-section geometry is illustrated in FIG. 5, with definition of the sides a and b. It will be noted that the channel cross-sectional area is given by A=4*a*b. The traveling wave grid moves charged particles effectively only within a layer of height h, where h is of the order of the electrode spacing of the grid. For the traveling wave grid to be able to remove all charged particles within this layer, the particles have to stay above the grid long enough to be moved from one side of the collection area to the other. This time, $t_2$, to move a particle across the width W of the channel is given by $$t_2 = \frac{W}{\mu E}$$

where E the electric field and μ=q/6πηr is the mobility of the bio-agent with charge q and radius r.

On the other hand, the particles move along the channel with the liquid flow. Because of a parabolic flow profile the particles will move slower closer to the wall than in the center of the channel. The fastest travel speed within the transport layer of the traveling wave grid is in the middle of the channel at the top of the layer and is given by:

$$u_{\max} = \frac{16A(-\partial p)}{\eta\pi^3}\sum_{i=odd}\frac{x(-1)^{(i-1)/2}}{i^3}\left(1-\frac{\cosh\left(\frac{i\pi(1-h/b)}{2x}\right)}{\cosh\left(\frac{i\pi}{2x}\right)}\right)$$

and particles within the transport layer will move across the grid with the (minimum) time $$t_1 = \frac{L}{u_{\max}}$$

where L is the length of the traveling wave grid. The condition to remove all charged particles from the transport layer is then given by $t_2=t_1$.

With A=4*a*b as the cross-sectional area of the channel (see FIG. 5), (−∂p) as the pressure gradient in the channel, and η as the dynamic viscosity of the solvent, the total flow rate of the liquid through the channel is given by $$Q = \frac{A^2(-\partial p)}{96\eta}C_Q(x)$$

where $C_Q(x)$ is a constant that depends only on the ratio x=a/b of the two sides. For channels with constant cross-sectional area $C_Q(x)$ is largest for a square channel, and decreases rapidly when one side becomes smaller/larger than the other. The same is true for $u_{max}$ hereinabove.

Table 1 lists system parameters for various channel geometries. It is assumed that the particles have a mobility of $1.7*10^{-8}$ $m^2/Vs$ (corresponding to particles of radius 5 nm and 10 electron charges, or 5 μm and 1000 charges). Particles with a higher mobility (those having a smaller r and/or larger charge) will respond more readily to the electric field and allow for even higher throughput. The length of the pre-concentrator is estimated from the flow rate for which all the particles near the traveling wave grid can be moved to the side chamber and represents the channel length needed to move a particle from the top of the channel through the center of the channel (where the flow velocity is at maximum). The channel length necessary for the pre-concentration step increases with flow rate, unless the channel width is increased, in which case the collection time with the traveling wave grids increases. The appropriate dimension for both is optimized depending on the required throughput rates and power availability.

TABLE 1

| Height [cm] | Width [cm] | Flow Rate [ml/s] | Time to screen 1 liter [min] | Diffusion distance for 10 nm particle [mm] | Diffusion distance for 10 μm particle [mm] | Length of pre-concentrator for 1000 V load voltage [m] |
|---|---|---|---|---|---|---|
| 0.5 | 0.5 | 0.81 | 20.2 | 0.09 | 0.01 | 1.12 |
| 0.5 | 1 | 0.9 | 17.6 | 0.12 | 0.01 | 0.59 |
| 0.5 | 2 | 1.01 | 16.0 | 1.76 | 0.02 | 0.29 |
| 0.5 | 5 | 1.13 | 14.8 | 2.8 | 0.03 | 0.11 |
| 0.5 | 10 | 1.16 | 14.3 | 3.9 | 0.04 | 0.06 |
| 1 | 1 | 3.3 | 5.1 | 0.12 | 0.01 | 4.4 |
| 1 | 2 | 3.8 | 4.4 | 0.18 | 0.02 | 0.95 |
| 1 | 5 | 4.3 | 3.9 | 0.28 | 0.03 | 0.92 |
| 1 | 10 | 4.5 | 3.7 | 0.39 | 0.04 | 0.18 |

To increase the amount of liquid that can be screened within a fixed time, throughput is maximized. This can be achieved by increasing the flow velocity $u_{flow}$, and/or increasing the cross-section of the channel. Both a decrease of W and an increase in $u_{flow}$ require an increase in L. (For a fixed speed $u_{tm}$, since $u_{tm}$ depends on the applied voltage and should not increase above ca. 1.5 V, i.e. E=1.5V/(grid electrode spacing) for platinum electrodes to avoid bubble formation, this parameter should not vary significantly.) It is also possible to increase the height H of the channel to increase throughput. However, in this case it is necessary to pre-concentrate the particles into a thin liquid layer of height h above the traveling wave grid, and to maintain a bias electric field to hold them close to the grid as the particles move through the channel. Both requirements can be satisfied by placing an electrode on top of the channel that provides the bias field.

Once the particles are moved to the side of the micro channel, they may be trapped inside a high-viscosity substance, such as a gel. This provides a medium where the particles will still be moved (at a lower speed), but are less subject to thermal diffusion that would be counteracting the concentration and focusing effort. The distance R a diffusing particle travels with time t is given by $$\langle R^2 \rangle = \frac{k_B T}{\pi \eta r} t$$

where $k_B$ is Boltzman's constant and T is the temperature. For bio-molecules with a radius of a few nanometers this distance is hundreds of microns per second in water. Therefore, a high viscosity medium such as a gel with effective viscosity 10 to 100 times larger than water is necessary to keep particles focused during and after the concentration step. For bacteria, which are about 1 micron in diameter, the diffusion distance is only a few microns per second, and none or a small increase in (effective) viscosity is sufficient to keep them in place for a few minutes. High viscosity media can be gels (poly-acryl amide, agarose, . . . ) for proteins and toxins, or micro-pore filters for viruses and bacteria. Micron-sized filters can also be made by etching a pillar structure into the substrate next to the flow channel. The liquid inside the pores of these materials does not change its viscosity. However, because of the interactions of the bio-agent with the gel or filter material they behave as if they are in a higher viscosity fluid.

Once the particles are inside the gel, the multi-dimensional concentration schemes discussed in U.S. patent application Ser. No. 10/727,289, "Concentration and Focusing of Bio-agents and Micron-sized Particles Using Traveling Wave Grids" may be applied. In particular, multiple traveling wave grids may be utilized to concentrate the charged bio agents into a well-defined spot and deliver them into a detector system. The extraction and delivery of the concentrated samples from high viscosity media to the detectors may be accomplished by syringe aspiration (viscous solution), heat melting and aspiration (agarose gel), electroblotting (poly-acrylamide gel), or other techniques known in the art.

The use of a traveling wave grid instead of a single electrode pair to move the particles into the gel has the advantage of enabling the generation of high local electric fields with small voltages (≈1V). Moreover, the field strength depends only on the inter-electrode spacing of the grid and is independent of the channel width. However, since the traveling wave field extends only a short distance into the liquid (about two thirds of the electrode spacing), a bias field is needed to push the particles towards the traveling wave grid and keep them there. A small voltage is sufficient to achieve this effect (0.1 V for a 100 μm thick channel—which translates into 1 V for a 1 mm high channel). Because the particle transport due to the traveling wave grid depends on the frequency of the traveling wave, the device may also be operated as a "high pass filter" which will only collect particles with mobilities above a threshold value.

Figure 6:
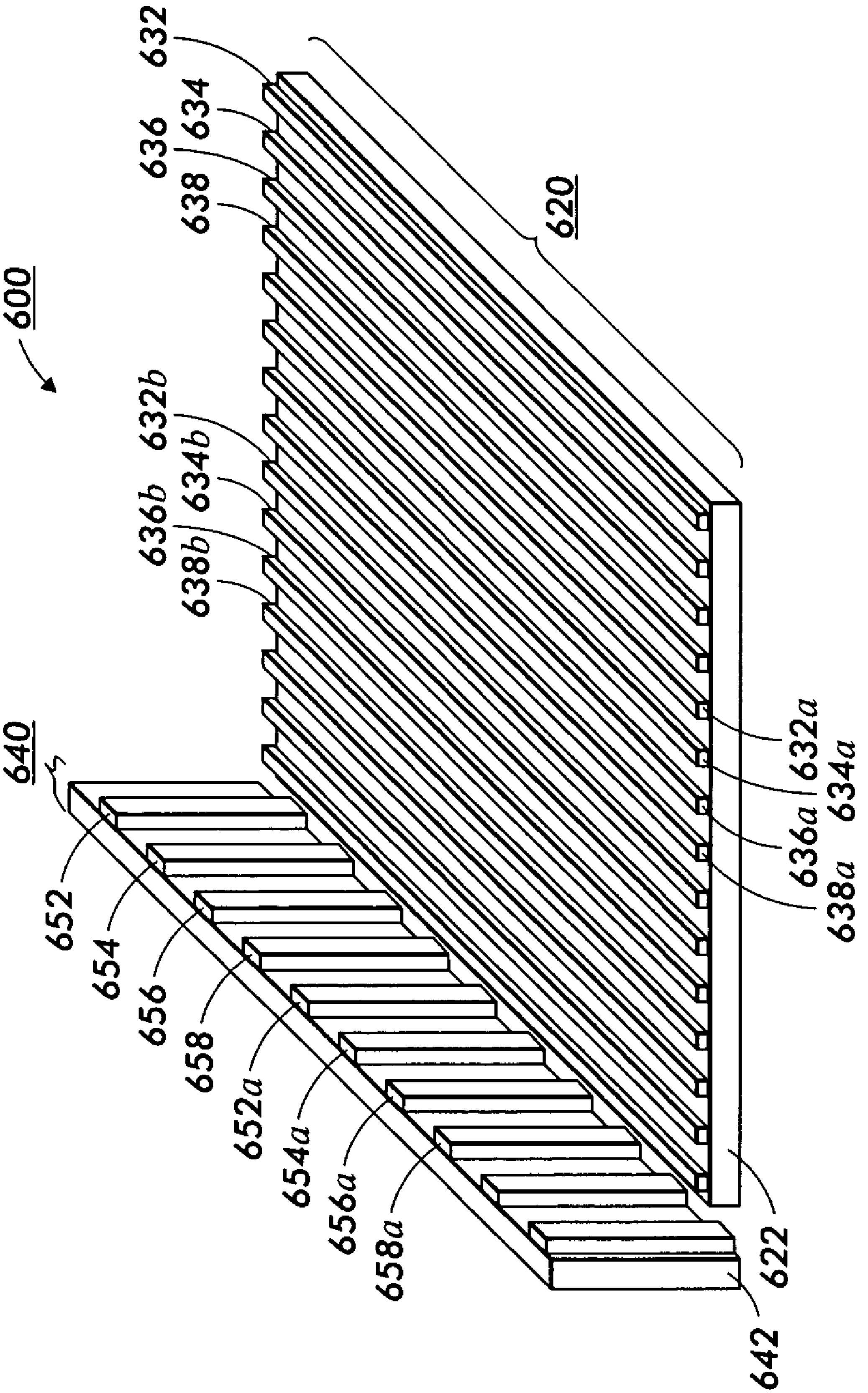
FIG. 6 is a schematic illustration of a system of traveling wave grids.

Referring to FIG. 6, a traveling wave grid system 600 is illustrated. The system 600 comprises a first traveling wave grid 620 including a substrate 622 and a plurality of electrodes 632, 634, 636, and 638; 632*a*, 634*a*, 636*a*, and 638*a*; and 632*b*, 634*b*, 636*b*, and 638*b*. The system 600 also comprises a second traveling wave grid 640 including a substrate 642 and a plurality of electrodes 652, 654, 656, and 658; and 652*a*, 654*a*, 656*a*, and 658*a*. The grids 620 and 640 are arranged at angles with respect to each other, within the ranges of 10° to 170°, 80° to 100°, or at 90°. In this configuration all charged particles that are within the reach of the electric field generated from grid 620 are moved to the wall of grid 640. That is, particles suspended above the grid 620 are transported toward the grid 640, which in FIG. 6, is towards the left side of the grid 620. The grid 640 moves the particles along the corner or region of intersection of the grids 640 and 620, and concentrates the particles either in one region that is determined by the pulse sequence of the waveform or at one of the ends of grid 640, such as where a detector is placed. If diffusion of the particles is sufficiently suppressed (e.g. by using a high-viscosity transport medium), the particles will remain confined in a small area near the corner of the grids, and the second grid 640 can concentrate them into a single small region, i.e. typically less than 1 $mm^3$.

Figure 7:
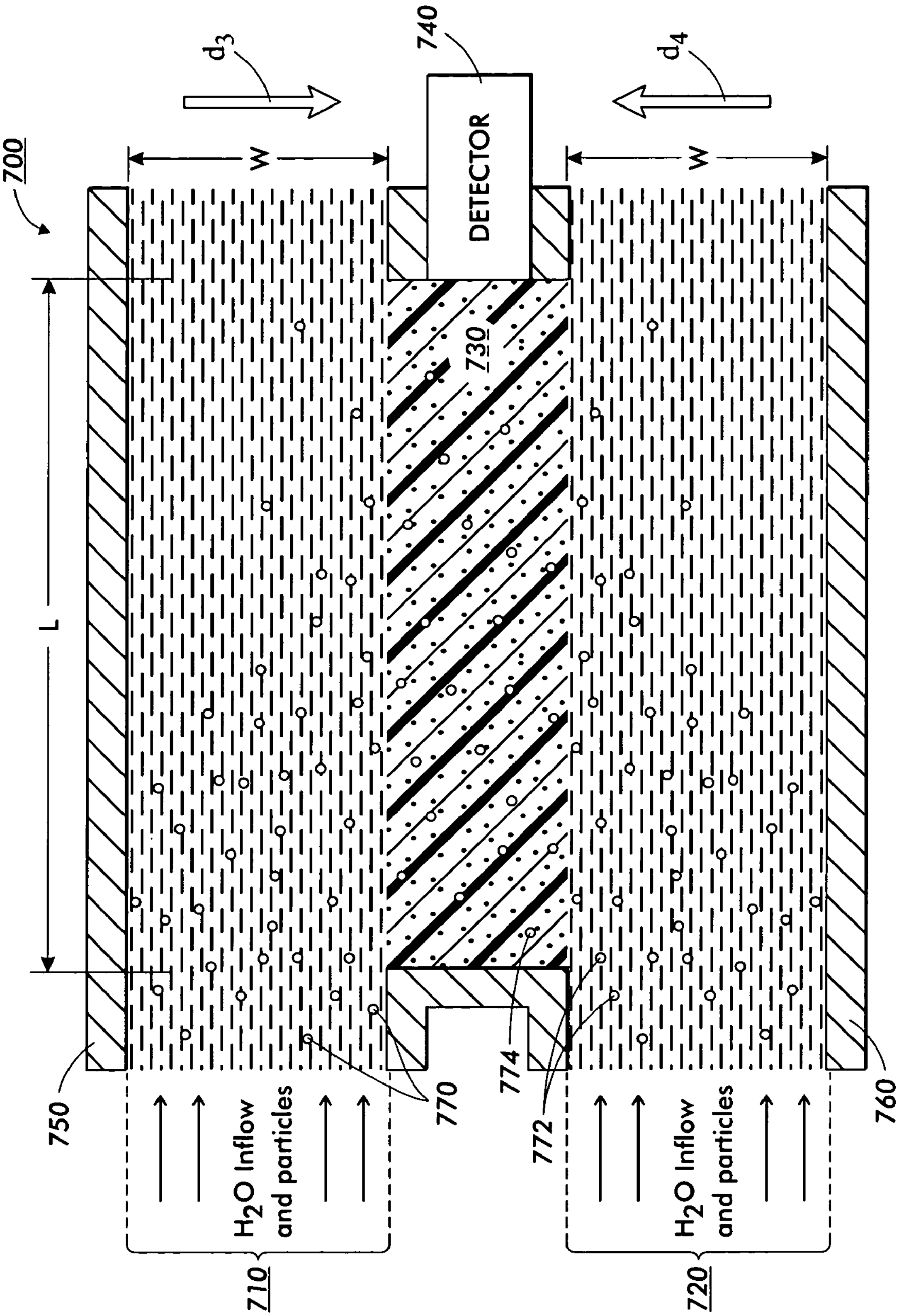
FIG. 7 is a schematic illustration of another embodiment of the continuous flow particle concentrator.

Turning now to FIG. 7, in an alternate embodiment the flow rate through the particle concentrator 700 may be increased through the use of two parallel channels separated by a capture area. In this embodiment, the liquid is passed left to right through flow channels 710 and 720. Charged bio-agents are removed from the liquid by concentrating them into a thin "transport" layer within the inlets to channels 710 and 720. This concentration from three to two dimensions may be achieved by use of electrostatic forces, geometric constraints, or a combination of both. The height of this transport layer depends on the reach of the traveling wave grid and is approximately the same as the electrode spacing of the grid. Once the particles 770 and 772 are concentrated within the transport layer, they pass across coplanar traveling wave grids (not shown) having a length L and width W that move the particles to an intermediate region between the two channels through application of traveling waves in opposing directions $d_3$ and $d_4$. The electrodes of these traveling wave grids have their electrodes aligned parallel with the channel, hence moving the particles toward a third central coplanar traveling wave grid 730 having its electrodes perpendicular to the electrodes of the first two traveling wave grids. Particles 774 in the central region 730 are moved toward detector 740. Each of the traveling wave grids includes a substrate, a collection of closely spaced and parallel electrically conductive electrodes extending across the substrate, and a collection of buses providing electrical communication with the collection of electrodes. At the central region 730 the particles may be trapped in an optional high-viscosity medium.

Also included but not shown are at least one voltage controller which provides a multi-phase electrical signal to the collection of buses and electrodes of both the first and second traveling wave grids. The voltage controller is configured to apply the control signal to the first traveling wave grid and the second traveling wave grid such that the bio-agent particles within the fluid medium at least partially travel or migrate across the coplanar traveling wave grids in a direction generally perpendicular to the direction of the electrodes of the coplanar grids. Then the bio-agents further migrate through the fluid medium at least partially across the third traveling wave grid in a direction generally perpendicular to the direction of the third collection of electrodes disposed on the third traveling wave grid. By use of this system and preferably in this manner, a bio-agent or collection of bio-agents, or collection of particles, can be directed or focused into a relatively highly concentrated region.

Figure 8:
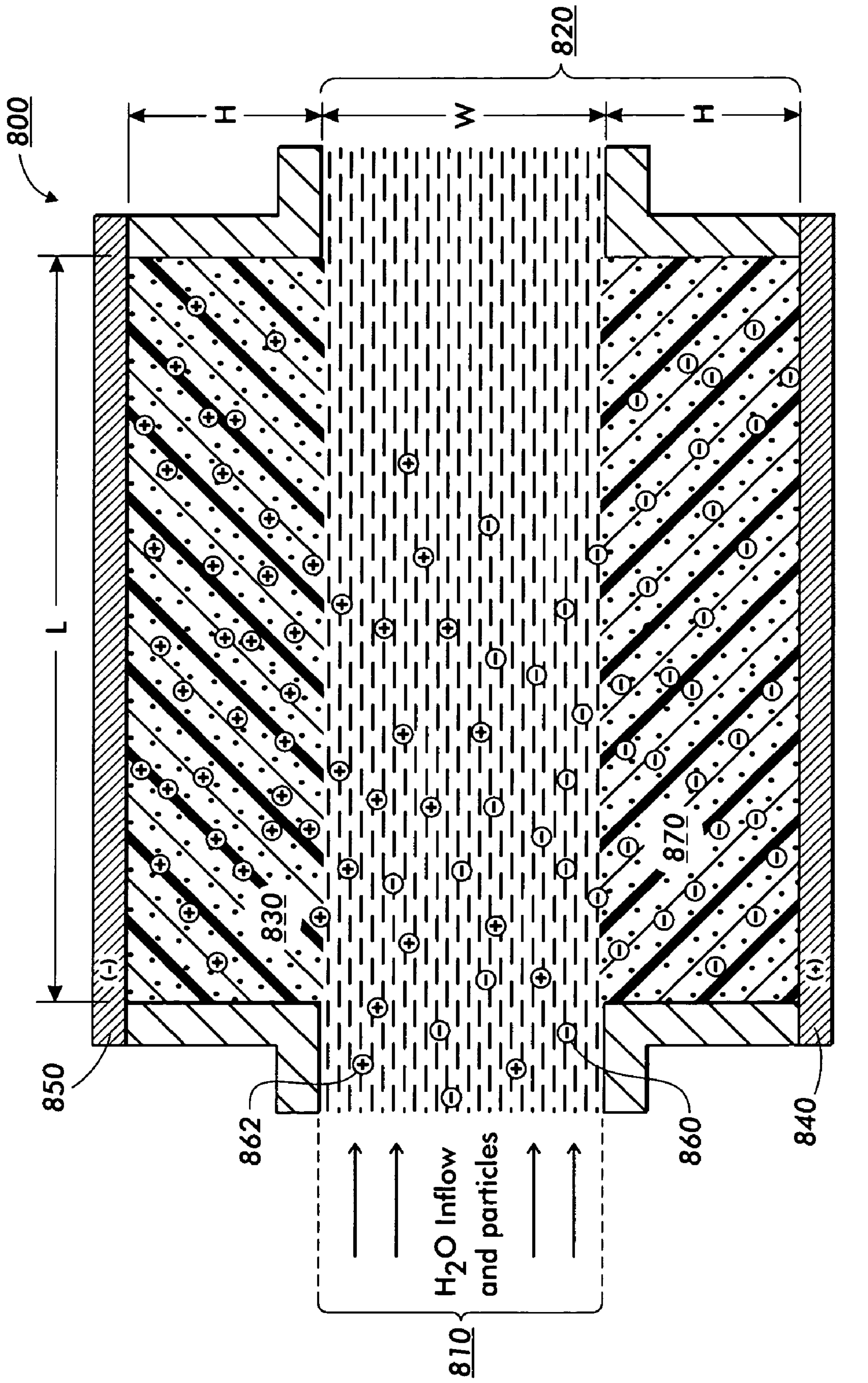
FIG. 8 is a schematic illustration of yet another embodiment of the continuous flow particle concentrator.

Bio-agents may also be separated and concentrated through charge differentiation, as illustrated in the embodiment of FIG. 8. In this embodiment of particle concentrator 800, the liquid is passed left to right through channel 810. Charged bio-agents are removed from the liquid by concentrating them into a thin "transport" layer at the bottom of channel 810. This concentration from three to two dimensions may be achieved by use of electrostatic forces, geometric constraints, or a combination of both. The height of this transport layer depends on the reach of the traveling wave grid and is approximately the same as the electrode spacing of the grid. Once the particles are concentrated within the transport layer, the particles of one charge pass across a traveling wave grid having a length L and a width W and are moved to one side of the channel, where they may be trapped into an optional high-viscosity medium 870 as shown with particle 860. An additional traveling wave grid 840 can then further focus the bio-agents trapped in the optional high viscosity medium 870 and move them to a detector or array of detectors (not shown). In this embodiment the traveling wave grid is operated with an appropriate voltage pattern, such that oppositely charged particles will travel in opposite directions. Here positively charged particles 862 are moved to one side of the flow channel, and negatively charged particles 860 are moved to the other side of the flow channel. Therefore, there will be two concentration areas, one on each side of the channel. Oppositely-charged particles 860 are trapped into an alternate optional high-viscosity medium 830. An additional traveling wave grid 850 can then further focus these bio-agents and move them to a detector or array of detectors (also not shown).

In a variation of the embodiment shown in FIG. 8, bio-agents of different charge are caused to migrate to separate concentration areas. This alternate configuration utilizes one traveling wave grid at the bottom of the flow channel and a second traveling wave grid at the top of the flow channel. The two grids provide the mutual bias voltage to move one-signed particles into a thin "transport" layer at the bottom of channel 810, the oppositely charged particles into a thin "transport" layer at the top of channel 810. In this embodiment the traveling wave grids are operated with appropriate voltage patterns, such that oppositely charged particles will travel in opposite directions The additional traveling wave grids 840 and 850 include substrates, a plurality of closely spaced and parallel electrically conductive electrodes extending across the substrates, and a collection of buses providing electrical communication with the collection of electrodes on the substrates of the additional traveling wave grid. Also included but not shown is at least one voltage controller, which provides a multi-phase electrical signal to the collection of buses and electrodes of both the first and additional traveling wave grids. The voltage controller is configured to apply the control signal to the first traveling wave grid and the additional traveling wave grids such that the bio-agent particles within the fluid medium at least partially travel or migrate across the first traveling wave grid in directions generally perpendicular to the direction of the electrodes of the additional grids. Then the bio-agents further migrate through the fluid medium at least partially across the additional traveling wave grids in a direction generally perpendicular to the direction of the collection of electrodes disposed on the first traveling wave grid. By use of this system and preferably in this manner, a bio-agent or collection of bio-agents, or collection of particles, can be directed or focused into separate relatively highly concentrated regions.

Figure 9:
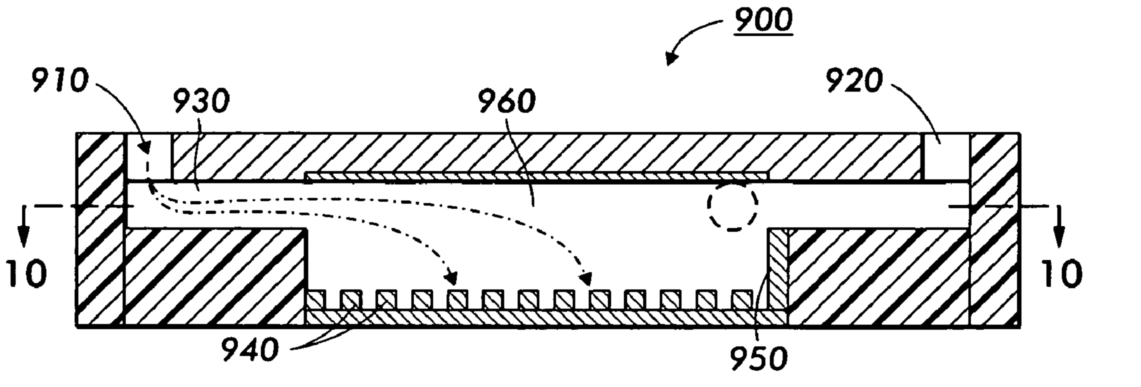
FIG. 9 is a cross-sectional view of another embodiment of the continuous flow particle concentrator utilizing field flow fractionation.

Turning now to FIG. 9, another embodiment of the device, using field flow fractionation (FFF) is illustrated. In this embodiment 900, a sample volume flows through a much smaller concentration cavity over a period of time. Flow 910 inlet is designed to have purely laminar flow into narrow cavity 930, with fluid expansion into a wider cavity 960 to reduce flow velocity thus allowing more time for the particles to respond to the applied electric field of traveling wave grid 940. Also, the vortex or re-circulation created at the bottom right corner of the flow cell directs the fluid flow towards the particle concentration area, thus keeping the sampled particles tightly focused. A transverse (vertical) electric field is applied to deflect bio-particles in the flow stream down towards to a TW grid 940 on the floor of the recessed cavity. TW voltages then move bio-particles to the right wall where an orthogonal TW grid 950 (illustrated further with respect to FIG. 10 herein below) concentrates the bio-particles to one corner for sample collection. The sample is released through outlet 920.

In this embodiment, to satisfy flow considerations, a 90 degree bend at the inlet 910 prevents angled flow impingement and produces a laminar flow with minimum in-plane flow component at the TW grid. The expansion into cavity 960 allows for slower flow velocity and therefore a lower requirement for bias deflection voltage and shorter TW dimension. The recessed cavity also acts to trap bio-particles.

Gravity may be sufficient to maintain the slow velocities, rendering a pump unnecessary.

In this embodiment charged particles deposit on traveling wave grid 940 in bands specified by their mobility or charge over size, with the higher mobility particles forming bands more to the left. Depending on the medium above the grid and the desired application, charged particles may be either accumulated in a single line at one end of the grid, or in individual lines parallel to the grid depending on specific parameters of the particles and the type of waveform applied to the traveling wave grid. By combining two traveling wave grids such that the electrodes of the two grids extend in a perpendicular fashion to each other, the particles may be further concentrated into a single region. To achieve a higher particle concentration, the focusing may be performed in a high-viscosity medium, e.g. a gel.

Referring further to FIG. 9, in one embodiment, grid 940 concentrates the particles in line(s) parallel to its electrodes. The extent and manner of concentration depends on the pulse sequence and transport medium properties. Grid 950 concentrates the particles further into one or more individual regions of relatively high particle concentration. Because the effectiveness of a traveling wave grid decreases the further the particles are located from its electrodes, a biasing grid can provide a bias voltage to keep the particles in a thin layer just above the active grid and can also maintain a bias voltage to keep the particles from escaping from this layer while they are undergoing transport.

Figure 10:
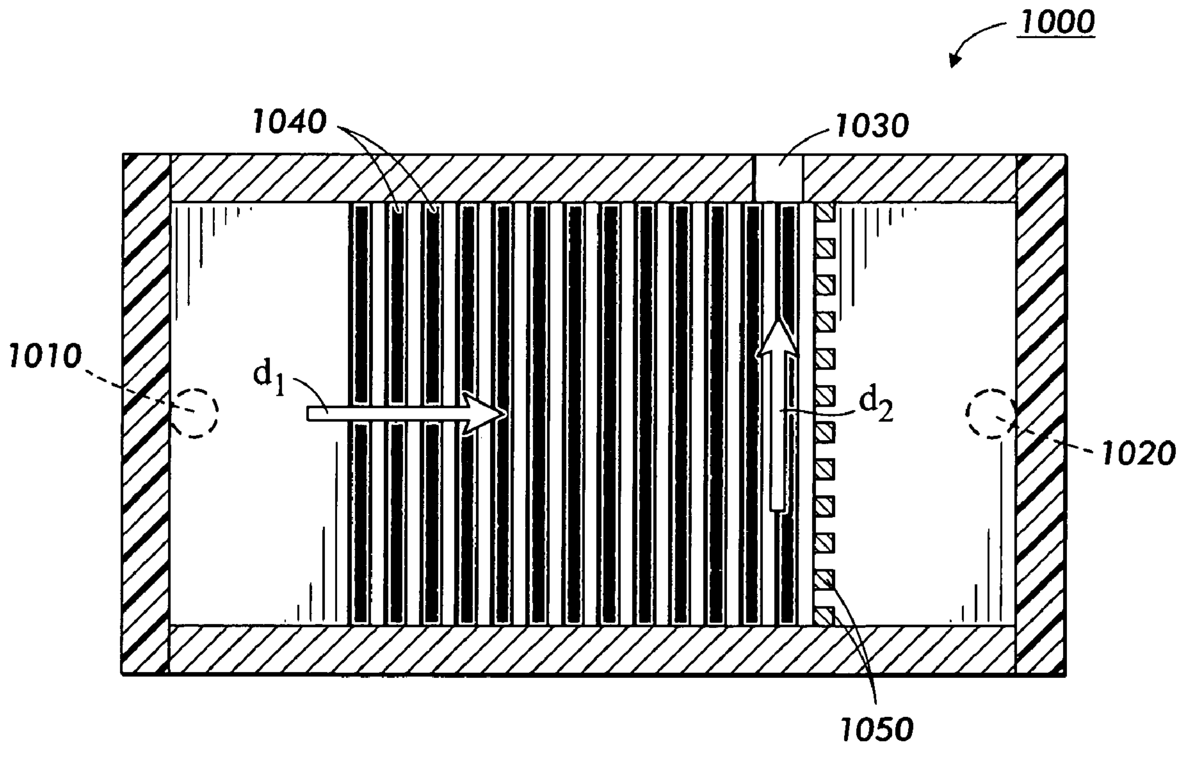
FIG. 10 is a schematic illustration of the embodiment of FIG. 9.

Turning now to FIG. 10, a schematic of the embodiment of FIG. 9 further illustrates flow patterns within this embodiment of the sample concentrator 1000. A sample volume enters the device at inlet port 1010 and moves into the expansion cavity in which traveling wave grid 1040 moves particles in direction $d_1$ toward orthogonally oriented traveling wave grid 1050, which moves particles in direction $d_2$ toward sample collection port 1030. The sample volume then exits at outlet 1020.

While the present discussion has been illustrated and described with reference to specific embodiments, further modification and improvements will occur to those skilled in the art. For example, any of the embodiments described herein could be utilized to operate the traveling wave grid as a high pass filter to collect only those particles with mobilities above a threshold value. Additionally, the bio-agents to be collected may be pre-selected through customization of traveling wave grid parameters, such as pulse sequence or frequency. The concentrator may operate on a single volume sample or continuous flow of a larger volume and may also utilize recirculation to ensure that all bio matter is deposited onto the collection plate. It is to be understood, therefore, that this disclosure is not limited to the particular forms illustrated and that it is intended in the appended claims to embrace all alternatives, modifications, and variations which do not depart from the spirit and scope of the embodiments described herein.

What is claimed:

1. An apparatus for extracting and concentrating bioagents within a continuously flowing fluid medium, the apparatus comprising:

at least one flow channel having a fluid inlet, wherein the bioagents are concentrated from three dimensions to a two-dimensional transport layer in a preconcentration area through application of at least one member selected from the group consisting of electrostatic forces, hydrodynamic forces, and geometric constraints;

at least two traveling wave grids, wherein a first traveling wave grid causes said concentrated bioagents to migrate to at least one specified side of said flow channel and a second traveling wave grid causes said concentrated bioagents to migrate from said at least one specified side of the flow channel to at least one extraction port, said at least two traveling wave grids comprising:

a substrate;

a collection of closely spaced and parallel electrically conductive electrodes extending across said substrate; and a collection of buses providing electrical communication with said collection of conductive electrodes;

at least one voltage controller for providing a multiphase electrical signal to said collection of buses and said collection of electrodes of said at least two traveling wave grids; and at least one flow channel outlet port.

2. The apparatus for extracting and concentrating bioagents according to claim 1, wherein said collection of electrodes is driven in a four phase voltage waveform having a ninety degree separation between said phases.

3. The apparatus for extracting and concentrating bioagents according to claim 2, wherein said waveform is a square wave pulse wherein each pulse is sequentially applied to an adjacent electrode in said collection of electrodes.

4. The apparatus for extracting and concentrating bioagents according to claim 3, further comprising means for customizing said pulse sequence or frequency to preselect specified types of bioagents.

5. The apparatus for extracting and concentrating bioagents according to claim 1, wherein said transport layer has a specified height, wherein said height is the order of the electrode spacing of the grid.

6. The apparatus for extracting and concentrating bioagents according to claim 1, further comprising a high viscosity medium applied to the flow surface of said second traveling wave grid.

7. The apparatus for extracting and concentrating bioagents according to claim 6, wherein said high viscosity medium comprises at least one member selected from the group consisting of gels and micro-pore filters.

8. The apparatus for extracting and concentrating bioagents according to claim 1, further comprising means for removal of said collected bioagents from said extraction port, wherein removal comprises at least one member selected from the group consisting of syringe aspiration, heat melting with aspiration, and electroblotting.

9. The apparatus for extracting and concentrating bioagents according to claim 1, wherein said first and second traveling wave grids are arranged at angles with respect to each other.

10. The apparatus for extracting and concentrating bioagents according to claim 9, wherein said angles have a range, said range extending from 10° to 170°.

11. The apparatus for extracting and concentrating bioagents according to claim 9, wherein said angles have a range, said range extending from 80° to 100°.

12. The apparatus for extracting and concentrating bioagents according to claim 9, wherein said angle is approximately 90°.

13. The apparatus for extracting and concentrating bioagents according to claim 1, wherein said at least two traveling wave grids comprise three traveling wave grids.

14. The apparatus for extracting and concentrating bioagents according to claim 13, wherein said three traveling wave grids are coplanar.

15. The apparatus for extracting and concentrating bioagents according to claim 14, further comprising one flow channel forming a central region and having a fluid inlet port, a fluid outlet port, and a first traveling wave grid located parallel to and between a second traveling wave grid and a third traveling wave grid.

16. The apparatus for extracting and concentrating bioagents according to claim 15, wherein said first traveling wave grid includes means for causing oppositely charged bioagent particles to migrate to specified opposing sides of said flow channel.

17. The apparatus for extracting and concentrating bioagents according to claim 13, wherein a first traveling wave grid is located parallel to and opposed to a second traveling wave grid and a third traveling wave grid is positioned orthogonally to said first traveling wave grid and said second traveling wave grid.

18. The apparatus for extracting and concentrating bioagents according to claim 17, wherein said first traveling wave grid and said second traveling wave grid are oppositely charged, and wherein said first traveling wave grid includes means for causing bioagents having a first charge to migrate toward said third traveling wave grid and said second traveling wave grid includes means for causing bioagents having a second charge to migrate toward said third traveling wave grid, and wherein said third traveling wave grid includes means for causing said bioagents having a first charge and said bioagents having a second charge to migrate to at least one extraction port.

19. The apparatus for extracting and concentrating bioagents according to claim 1, wherein said flow channel includes a narrow portion adjacent to said inlet port and a wider cavity to permit fluid expansion over said first traveling wave grid.

20. The apparatus for extracting and concentrating bioagents according to claim 19, further comprising means for depositing the paticles in individuals bands according to their mobility or charge over size.

21. The apparatus for extracting and concentrating bioagents according to claim 1, further comprising means for causing a previously processed fluid sample to be reprocessed to capture any bioagents remaining in the sample.

22. The apparatus for extracting and concentrating bioagents according to claim 1, wherein said bioagent particles have mobilities, further comprising means for customizing said pulse sequence or frequency to collect only particles with mobilities above a specified value.

23. An apparatus for extracting and concentrating bioagents within a continuously flowing fluid medium, the apparatus comprising:

at least two flow channels having a fluid inlet wherein the bioagents are concentrated from three dimensions to a two-dimensional transport layer in a preconcentration area through application of at least one member selected from the group consisting of electrostatic forces, hydrodynamic forces, and geometric constraints;

a central region located parallel to and between said at least two flow channels, wherein a first flow channel includes a fluid inlet port, a fluid outlet port, and a first traveling wave grid, a second flow channel includes a second fluid inlet port, a second fluid outlet port, and a second traveling wave grid, and said central region comprises a third traveling wave grid;

at least three traveling wave grids, wherein said first traveling wave grid causes said concentrated bioagents to migrate to at least one specified side of said first flow channel and said second traveling wave grid causes said concentrated bioagents to migrate to at least one specified side of the second flow channel, said three traveling wave grids are coplanar and comprising:

a substrate;

a collection of closely spaced and parallel electrically conductive electrodes extending across said substrate; and a collection of buses providing electrical communication with said collection of conductive electrodes;

at least one voltage controller for providing a multiphase electrical signal to said collection of buses and said collection of electrodes of said at least two traveling wave grids; and at least two flow channel outlet port.

24. The apparatus for extracting and concentrating bioagents according to claim 23, wherein said first traveling wave grid includes means for causing said concentrated bioagents to migrate to a specified side of said first flow channel toward said central region, said second traveling wave grid includes means for causing said concentrated bioagents to migrate to a specified side of said second flow channel toward said central region, and said third traveling wave grid includes means for causing said concentrated bioagents to migrate to a specified end of said central region, wherein is located at least one extraction port.

* * * * *